United States Patent
Evans

(10) Patent No.: US 6,323,368 B1
(45) Date of Patent: Nov. 27, 2001

(54) PROCESS

(75) Inventor: Graham Evans, Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/452,012

(22) Filed: Nov. 30, 1999

(30) Foreign Application Priority Data

Dec. 2, 1998 (GB) .................................................. 9826540

(51) Int. Cl.[7] .................................................. C07C 211/00
(52) U.S. Cl. .......................... 564/307; 564/304; 564/305; 564/308
(58) Field of Search ..................... 564/304, 307, 564/305

(56) References Cited

U.S. PATENT DOCUMENTS 3,830,934   8/1974   Flick et al. ........................... 564/304
5,723,668   3/1998   Buschmann et al. ................. 424/330

OTHER PUBLICATIONS

Frankus, Von E. et al. (1978) "Über die Isomerentrennung, Strukturaufklärung und pharmakologische Charakterisierung von 1–(m–Methoxyphenyl)–2–(dimethylaminomethyl) cyclohexan–1–ol" *Drug Res.* 28(1):114–121.

*Primary Examiner*—Gary Geist
*Assistant Examiner*—Leigh C. Maier
(74) *Attorney, Agent, or Firm*—Saliwanchik, Lloyd & Saliwanchik

(57) ABSTRACT

A process for preparing a substantially single enantiomer of tramadol, or a pharmaceutically-acceptable salt thereof, proceeds by means of a classical salt resolution using a substantially single enantiomer of O,O-di-p-toluoyltartaric acid as a resolving agent.

14 Claims, No Drawings

PROCESS

FIELD OF THE INVENTION

The present invention relates to a process for the manufacture of single enantiomers of tramadol.

BACKGROUND TO THE INVENTION

Tramadol (cis-2-dimethylaminomethyl-1-(3-methoxyphenyl)-1-cyclohexanol) is a chiral drug substance which is used as a high-potency analgesic agent. Although tramadol is currently marketed as the racemate only, there has been considerable interest in the physiological properties associated with its individual enantiomers, namely 1S, 2S-(−)-tramadol and 1R, 2R-(+)-tramadol, the latter shown below as (1). For example, lead references to literature on this topic are highlighted in WO-A-9840053. It is possible that further investigations in this field will lead to a better understanding of the pharmacology of tramadol enantiomers, which could in turn allow for improved pharmaceutical compositions to be identified.

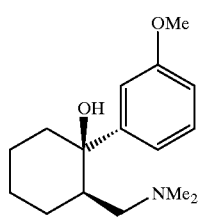

(1)

In connection with our own interest in this area, we required an efficient and reliable method for the preparation of individual enantiomers of tramadol. Due to the ready availability of racemic tramadol a classical resolution process, involving separation of diastereomeric salts by selective crystallisation, appeared ideal for this purpose.

Initially, literature procedures for the resolution of tramadol were investigated. In U.S. Pat. No. 5,723,668, it is reported that use of L-(+)-tartaric acid as resolving agent facilitates a highly efficient resolution whereby 49% yield (with respect to racemic base) of a diastereomerically-pure salt of 1S, 2S-(−)-tramadol is obtained after a single crystallisation from ethanol solution, by filtration and washing with solvent. However, in our hands, these results could not be reproduced. Typically, following dissolution of racemic tramadol and L-(+)-tartaric acid, we observed crystallisation, but analysis of the isolated salt showed little or no diastereomeric enrichment.

Another resolution process is described in U.S. Pat. No. 3,830,934, in which O,O-dibenzoyl-D-tartaric acid is used as resolving agent. Our own investigation of this process indicated that at least three cycles of dissolution-crystallisation-filtration are required in order to obtain salt of >98% de (diastereomeric excess), corresponding to >98% ee (enantiomeric excess) tramadol free base after cracking. Thus the process may be suitable as a small-scale preparative method. However, the need for multiple crystallisation cycles with cumulative lowering of yields may render the process unsuitable and economic for operation on a larger scale, e.g. for manufacturing processes.

SUMMARY OF THE INVENTION

This invention is based on the discovery that racemic tramadol can be resolved efficiently using the substantially single enantiomers of O,O-di-p-toluoyltartaric acid (DTTA) as a revolving agent. This resolving agent may also be used to increase the optical purity of enantiomerically-enriched tramadol, i.e. tramadol which is already enriched in one of its two enantiomers.

DESCRIPTION OF THE INVENTION

The process of this invention may be carried out under conditions that are generally known to those skilled in the art of classical resolution methods. The resolution process is extremely simple. In a typical example, dissolution of tramadol free base and O,O-di-p-toluoyl-L-tartaric acid (1 molar equivalent) by warming in ethanol, followed by cooling, gave crystallisation in 47% yield (based on racemic tramadol) of a diastereomeric salt enriched in (−)-tramadol, with a de of 97%, corresponding to 97% ee tramadol. This salt was reslurried in ethanol, and then filtered, washed and dried, which resulted in an enhanced de of 99.5%. Thus, in contrast to the multiple cystallisation cycles required when O,O-dibenzoyltartaric acid is used as the resolving agent, the present process allows diastereomericallly pure salts to be isolated in high yield after a single cystallisation from solution. It is surprising that what may be regarded as a small structural difference between O,O-dibenzoyltartaric acid and O,O-di-p-toluoyltartaric acid, i.e. aromatic hydrogen atoms, remote at positions from the chiral centres, replaced by methyl groups, results in such a dramatic improvement in the efficiency of the resolution process.

Any suitable solvent may be used to effect the process of the present invention. Preferred solvents are $C_{1-4}$ alkanols, of which ethanol is especially preferred.

Since both enantiomers of the resolving agent are readily available in quantity, either can be used to effect resolution, depending on the which enantiomer of tramadol is required. For example O,O-di-p-toluoyl-L-tartaric acid gives initial crystallisation of a diastereomeric salt enriched in (−)-tramadol, whereas with O,O-di-p-toluoyl-D-tartaric acid a diastereomeric salt enriched in (+)-tramadol is obtained. When both enantiomers of tramadol are required, these processes can be combined in a so-called "mirror image" resolution whereby after crystallisation of, say, a diastereomeric salt of (−)-tramadol and O,O-di-p-toluoyl-L-tartaric acid, mother liquors remaining are processed to isolate residual tramadol free base enriched in the (+)-enantiomer, which is then purified further by treatment with O,O-di-p-toluoyl-D-tartaric acid and crystallisation of the resultant salt.

Other beneficial aspects of the process of the present invention have been identified and these can be summarised as follows:

1. The O,O-di-p-toluoyltartaric acid resolving agent can be easily recovered in a state of high purity, such that it can be re-used in one or more subsequent resolution processes.
2. Typically, 1 molar equivalent of the O,O-di-p-toluoyltartaric acid is used relative to racemic tramadol free base. However, if desired, less than 1 molar equivalent may be used, e.g. as little as 0.50 molar equivalent, preferably around 0.5–0.6 molar equivalents, such that the yield of diastereomeric salt obtained on initial crystallisation is comparable to that achieved with 1 equivalent of resolving agent, leaving an excess of tramadol free base in solution. Isolated diastereomeric salts obtained by either method have a 1:1 stoichiometry of resolving agent:tramadol.
3. Efficient resolution can be achieved when the feedstock of racemic tramadol is contaminated with isomeric trans-2-dimethylaminomethyl-1-(3-methoxyphenyl)-1-cyclo-hexanol, which may be formed in levels of up to 10–20% during the manufacture of the former.

In the context of this Application, by a substantially single enantiomer typically we mean that one of the enantiomers is present in an excess of at least 70%, preferably at least 90%, and more preferably at least 95%, with respect to its opposite enantiomer, including an optically-pure enantiomer.

The present invention is further illustrated by the following examples.

EXAMPLES

Example 1

Resolution of (+/−)-Tramadol with Di-p-toluoyl-L-tartaric Acid in Ethanol 57 g of racemic Tramadol hydrochloride (0.190 mol) was taken up in 110 mls of distilled water. To this yellow coloured solution is added 120 ml of dichloromethane, and the reaction mixture stirred at 10° C. in a jacketed vessel. A solution of 36% sodium hydroxide 22 ml is added dropwise to the tramadol hydrochloride. After 10 minutes stirring the layers are allowed to separate, and the bottom organic layer removed. The basic aqueous layer is re-extracted with 35 ml of dichloromethane and combined with the first organic layer. These are then washed with water 100 ml. Concentration of the organic layers under vacuum gives the racemic tramadol free base in quantitative yield (50 g) as a yellow oil. The free base is taken up in 200 ml of ethanol and this solution is added to the Di-p-toluoyl-L-tartaric acid ((L)-(−)-DTTA) 73.4 g (0.190 mol) in 700 ml of ethanol at 70° C. On cooling to 65° C. a precipitate forms. The resolution is gradually cooled to 25° C. and left to age over a period of approximately fifteen hours.

The copious white precipitate that formed was collected by filtration, washing with 200 ml of ethanol. This gave after drying 57.8 g (46.8%) of (−)-Tramadol. Di-p-toluoyl-L-tartaric acid with a de of 96.8% (chiral HPLC). Repetition of the above procedure gave 58.6 g (47.5%) of the same salt with a de of 97.5%. These salts were combined and reslurried in 575 ml of ethanol to give 111.6 g of the (−)-Tramadol containing salt, with a de of >99.5% in 97.0% yield. $[\alpha]_D^{589}=-104.9°$ (C=1.36, MeOH). MP =167.5–168.0° C. (DSC). Evaporation of the mother liquors from the two resolutions above gave a slightly coloured oil 131 g (53.1%), of (+)-Tramadol. Di-p-toluoyl-L-tartaric acid salt with a de of ~89.5%.

Example 2

Resolution of (+)-enantiomer-enriched Tramadol with Di-p-toluyl-D-tartaric Acid in Ethanol The (+)-Tramadol-containing salt from Example 1 was cracked using 2.1 equivalents of sodium hydroxide as follows. The (+)-Tramadol. (L)-(−)-DTTA salt 131 g (0.202 mol) in 1 volume of ethanol was taken up in 150 ml of dichloromethane and placed in a jacketed vessel at 10° C. To this yellow coloured solution was added water 300 ml and the mixture stirred. To this mixture was added a solution of 16.8 g sodium hydroxide (0.423 mol) in 200 ml of distilled water dropwise with stirring. The layers were then separated, the bottom organic layer collected. The basic aqueous layer was re-extracted with 150 ml of dichloromethane. The organic layers were combined and washed with water 200 ml before concentrated to dryness. This gave approximately 53 g of Tramadol free base enriched in the (+)-enantiomer as a slightly coloured oil. The basic aqueous layer was acidified with hydrochloric acid to pH=2.0, and the acidic aqueous solution extracted with 300 ml of tert-butylmethylether (TBME). Concentration of the TBME solution gave a slightly coloured oil in quantitative yield. This was taken up in 150 ml of iso-propanol and heated to reflux. To this refluxing solution was added 350 ml of heptane, which effected crystallisation. The crystallisation was left to cool to ambient temperature and age overnight.

The white solid was collected by filtration to give 58.3 g (75.4%) of (L)-(−)-DTTA which compared to an authentic sample. 77.3 g of Di-p-toluoyl-D-tartaric acid ((D)-(+)-DTTA) was taken up in 550 ml of ethanol at 70° C. in a jacketed vessel. To this solution was added the Tramadol free base in 200 ml of ethanol. A precipitate formed almost immediately. The vessel was gradually cooled to 25° C. over several hours to give a fine white solid. Stirring at 25° C. was maintained overnight. The resulting copious white solid was collected at the pump, washing with 500 ml of ethanol. This gave 111.6 g of (+)-Tramadol. Di-p-toluoyl-D-tartaric acid in 85.2% yield, with a de of 97.3%. Reslurrying of this salt from 500 ml of ethanol as above gave 108.5 g of the (+)-Tramadol-containing salt, with a de of >99% in 97.8% yield. $[\alpha]_D^{589}=+103.30°$ (C=1.15, MeOH). MP=162.1–167.8° C. (DSC).

Example 3

Resolution of (+/−)-Tramadol with Recovered Di-p-toluoyl-L-tartaric Acid in Ethanol 11.4 g of racemic Tramadol hydrochloride was converted to the racemic tramadol free base in quantitative yield (10 g) as a yellow oil using the same procedure outlined in Example 1. The free base is taken up in 20 ml of ethanol and this solution is added to the Di-p-toluoyl-L-tartaric acid ((L)-(−)-DTTA) (which was recovered from a previous resolution) 14.7 g (0.038mol) in 120 ml of ethanol at 70° C. On cooling to 65° C. a precipitate forms. The resolution is gradually cooled to 25° C. and left to age over a period of approximately fifteen hours.

The copious white precipitate that formed was collected by filtration, washing with 60 ml of ethanol. This gave after drying 11.40 g (46.2%) of (−)-Tramadol. Di-p-toluoyl-L-tartaric acid salt with a de of 96.2% (chiral HPLC). Evaporation of the mother liquors gave a slightly coloured oil 13.50 g (>55%), of (+)-Tramadol. Di-p-toluoyl-L-tartaric acid salt with a de of 84.9%.

Example 4

Resolution of (+/−)-Tramadol with 0.55 Equivalents of Di-p-toluoyl-L-tartaric Acid in Ethanol 11.4 g of racemic Tramadol hydrochloride (0.038 mol) was converted to the racemic tramadol free base in quantitative yield (10 g) as a yellow oil using the same procedure outlined in Example 1. The free base is taken up in 10 ml of ethanol and this solution is added to the Di-p-toluoyl-L-tartaric acid ((L)-(−)-DTTA) 8.08 g (0.021 mol) 0.55 equivalents plus acetic acid 1.26 g (0.021 mol) in 40 ml of ethanol at 70° C. On cooling to 65° C. a seed sample was added which effected crystallisation. The resolution is gradually cooled to 25° C. and left to age over a period of approximately fifteen hours.

The copious white precipitate that formed was collected by filtration, washing with 10 ml of ethanol. This gave after drying 7.10 g (39.3%) of (−)-Tramadol. Di-p-toluoyl-L-tartaric acid salt with a de of 97.1% (chiral HPLC). Evaporation of the mother liquors gave a slightly coloured oil 12.50 g (>61%), of (+)-Tramadol. Di-p-toluoyl-L-tartaric acid salt with a de of 40.9%.

Example 5

(+)-Tramadol Hydrochloride Preparation from (+)-Tramadol.Di-p-toluyl-D-Tartaric Acid Salt 108 g of (+)-Tramadol.Di-p-toluyl-D-Tartaric acid salt obtained above de >99% was cracked according to Example 2, this gave 43 g of (+)-Tramadol free base. This enantiomerically-pure free base was taken up in 475 ml of butan-2-one in a jacketed vessel and set to stir at 20° C. To this solution was added 3.06 ml of distilled water in one go. After this 18.9 g, 22.1 ml of chlorotrimethyl-silane was added via syringe. The reaction was stirred at 20° C. overnight. The thus formed white precipitate was collected by filtration, washing with 175 ml of cold butan-2-one. The white solid was dried under vacuum at 70° C. to give 43.2 g (87.3%), ee >99%. $[\alpha]_D^{589}$=+34.3° (C=1.22, MeOH). MP =172.7–173.9° C.

Example 6

(−)-Tramadol Hydrochloride Preparation from (−)-Tramadol.Di-p-toluoyl-L-tartaric Acid Salt 111 g of (−)-Tramadol.Di-p-toluoyl-L-tartaric acid salt obtained above de =>99% was cracked according to Example 2. This gave 45 g of (−)-Tramadol free base. This enantiomerically-pure free base was taken up in 500 ml of butan-2-one in a jacketed vessel and set to stir at 25° C. To this solution was added 3.08 ml of distilled water in one go. After this 22.2 ml of chlorotrimethylsilane was added via syringe. The reaction was stirred at 20° C. overnight. The thus formed white precipitate was collected by filtration washing with 200 ml of cold butan-2-one. The white solid was dried under vacuum at 70° C. to give 47.0 g (92.0%), ee=>99%. $[\alpha]_D^{589}$=−34.3° (C=1.27, MeOH). MP=172.4–173° C.

Example 7

Attempted Resolution of (+/−)-Tramadol with (L)-(+)-tartaric Acid 60 g of (+/−)-Tramadol hydrochloride (0.0228 mol) were suspended in 96 ml of water and treated with 32 g of crushed ice. To this suspension was added 26 ml of 36% sodium hydroxide solution. The mixture was then extracted with dichloromethane 140 ml, followed by re-extraction with a further 40 ml of dichloromethane. The organic layers were combined and dried over magnesium sulphate. The solvent was then removed under vacuum to give the (+/−)-Tramadol free base quantitatively as a yellow oil. This was taken up in 48 ml of ethanol and added to a solution of 30 g (L)-(−)-tartaric acid (0.0228 mol) in 224 ml of ethanol. This solution was stirred at 20° C. for two hours, and then allowed to stand for 24 hours at 4° C.

After this time a copious amount of white precipitate had formed. This was collected by filtration and washed with 128 ml of cold ethanol. After drying approximately 77.6 g of the solid material had been obtained in 93.9% yield. Analysis by chiral HPLC indicated that this material was essentially racemic.

Further attempts were made to increase the diastereomeric excess by re-suspending in ethanol and stirring overnight at 25° C., this however failed. Likewise hot slurries in ethanol and methanol also did not affect de enhancement.

What is claimed is:

1. A process for preparing a substantially single enantiomer of tramadol, or a pharmaceutically-acceptable salt thereof, said process comprising resolving racemic tramadol by classical salt resolution using a substantially single enantiomer of O,O-di-p-toluoyltartaric acid as a resolving agent.

2. The process according to claim 1 for preparing substantially single enantiomer (+)-tramadol, or a pharmaceutically-acceptable salt thereof, which uses O,O-di-p-toluoyl-D-tartaric acid as the resolving agent.

3. The process according to claim 1 for preparing substantially single enantiomer (−)-tramadol, or a pharmaceutically-acceptable salt thereof, which uses O,O-di-p-toluoyl-L-tartaric acid as the resolving agent.

4. A process for increasing the optical purity of enantiomerically-enriched tramadol to substantially single enantiomer tramadol, said process comprising contacting enantiomerically-enriched tramadol with a substantially single enantiomer of O,O-di-p-toluoyltartaric acid.

5. The process according to claim 1, said process further comprising converting the salt obtained by the resolution to the free base form of tramadol, or a pharmaceutically-acceptable salt thereof.

6. A diastereometric salt of substantially single enantiomer tramadol and substantially single enantiomer O,O-di-p-toluoyltartaric acid.

7. The process according to claim 4, which further comprises conversion of the salt obtained by the resolution to the free base form of tramadol, or a pharmaceutically-acceptable salt thereof.

8. A process according to claim 1, wherein said racemic tramadol is contaminated with trans-2-dimethylaminomethyl-1-(3-methoxyphenyl)-1-cyclohexanol.

9. The process according to claim 1, wherein said substantially single enantiomer of tramadol produced by said process is in an excess of at least 70%, with respect to the opposite enantiomer.

10. The process according to claim 1, wherein said substantially single enantiomer of tramadol produced by said process in an excess of at least 90%, with respect to the opposite enantiomer.

11. The process according to claim 1, wherein said substantially single enantiomer of tramadol produced by said process in an excess of at least 95%, with respect to the opposite enantiomer.

12. The process according to claim 4, wherein said substantially single enantiomer of tramadol produced by said process in an excess of at least 70%, with respect to the opposite enantiomer.

13. The process according to claim 4, wherein said substantially single enantiomer of tramadol produced by said process in an excess of at least 90%, with respect to the opposite enantiomer.

14. The process according to claim 4, wherein said substantially single enantiomer of tramadol produced by said process in an excess of at least 95%, with respect to the opposite enantiomer.

* * * * *